United States Patent [19]

Wong

[11] Patent Number: 5,230,619
[45] Date of Patent: Jul. 27, 1993

[54] ORTHODONTIC APPLIANCE WITH PROTECTIVE POROUS FILM

[75] Inventor: Raymond F. Wong, Chino Hills, Calif.
[73] Assignee: Ormco Corporation, Glendora, Calif.
[21] Appl. No.: 892,263
[22] Filed: Jun. 2, 1992
[51] Int. Cl.$^5$ ............................................. A61C 3/00
[52] U.S. Cl. ........................................................ 433/9
[58] Field of Search ........................................ 433/8, 9

[56] References Cited

U.S. PATENT DOCUMENTS

| | | | |
|---|---|---|---|
| 4,068,379 | 1/1978 | Miller et al. | 32/14 A |
| 4,165,561 | 8/1979 | Miller et al. | 32/14 A |
| 4,172,323 | 10/1979 | Orlowski | 32/6 |
| 4,256,455 | 3/1981 | Forster | 433/8 |
| 4,360,342 | 11/1982 | Salvo | 433/172 |
| 4,433,960 | 2/1984 | Garito et al. | 433/215 |
| 4,479,527 | 10/1984 | Boettcher | 164/34 |
| 4,889,485 | 12/1989 | Iida | 433/9 |
| 4,904,188 | 2/1990 | Baurmash | 433/9 X |
| 4,927,361 | 5/1990 | Smith et al. | 433/9 |
| 4,948,366 | 8/1990 | Horn et al. | 433/9 |
| 5,078,597 | 1/1992 | Caplin | 433/9 X |
| 5,110,290 | 5/1992 | Wong | 433/9 |

OTHER PUBLICATIONS

Samir E. Bishara & Timothy S. Trulove "Comparisons of Different Debonding Techniques for Ceramic Brackets: An In Vitro Study" Aug., 1990, pp. 145–153.

Primary Examiner—Robert P. Swiatek
Assistant Examiner—Nicholas D. Lucchesi
Attorney, Agent, or Firm—Wood, Herron & Evans

[57] ABSTRACT

Orthodontic appliances are disclosed which have a base portion with a chemically active bonding surface and a protective porous mesh affixed to the bonding surface to prevent contamination thereof. Fabric-type mesh materials are contemplated for use as the protective film. The protective film is preferably inert to the orthodontic adhesives utilized to affix the bracket to a tooth.

6 Claims, 1 Drawing Sheet

ORTHODONTIC APPLIANCE WITH PROTECTIVE POROUS FILM

FIELD OF THE INVENTION

The present invention relates to orthodontic appliances such as orthodontic brackets having a chemically active bonding surface and a protective film thereon.

BACKGROUND OF THE INVENTION

Orthodontic appliances, and in particular orthodontic brackets, are made of various materials including ceramics (e.g., mono- or poly-crystalline alumina), plastics (e.g., polycarbonate), and metal. Non-metallic brackets are most commonly chemically bonded to the tooth enamel. In order to enhance the chemical bonding of a bracket to a tooth, it is known to provide the bracket with a chemically active bonding surface or bonding base which interacts with the chemical adhesive to form a suitably strong bond to a tooth. For example, U.S. Pat. Nos. 4,826,430 and 4,948,366 describe the preparation of ceramic brackets having chemically active bonding surfaces, and U.S. Pat. No. 4,673,354 discloses brackets made of porcelain, metal alloys and resin composites which have a chemically active layer.

A significant limitation of brackets which have a chemically active bonding base or surface is their sensitivity to contamination. To ensure the maximum desired bond strength, it is imperative that contact of the bonding surface with foreign matter be eliminated. Any contamination of the chemically active bonding surface causes physical hinderance of the molecular functionality thereof, which reduces chemical coupling (bond strength) by an amount generally corresponding or proportional to the degree of contamination. Since it is common to bulk package brackets with a chemically active surface, there is a significant risk of contamination as the brackets tumble about and contact one another during transportation and handling. Further potential for contamination is possible from finger contact as the brackets are removed from packaging and manipulated during chair side set-up by the clinician. Contamination of the chemically active bonding surface causes the contaminated regions to become effectively chemically "dead". It is believed that contamination thus deleteriously affects the integrity of the bond which is ultimately achieved, potentially resulting in clinically unacceptable bonding of brackets to teeth. Poor bonding may result in failure during the course of the orthodontic treatment, thereby necessitating return visits to the orthodontist for replacement/reattachment of brackets.

SUMMARY OF THE INVENTION

The present invention overcomes the various shortcomings and provides a solution to many of the problems pointed out above with respect to orthodontic brackets having a chemically active bonding surface.

In general, the present invention is directed to an orthodontic appliance, such as a bracket, having a chemically active bonding base or surface and a protective porous film which is believed to substantially prevent contamination of the chemically active bonding surface. By effectively preventing contamination of the chemically active bonding surface, the protective porous film enables the clinician to apply brackets to teeth with confidence in the integrity and uniformity of the bond strength. The reduced bond failures will be realized since contaminants are believed to be retained on the protective film and ultimately encapsulated in the adhesive without "deadening".

Certain characteristics of the porous film are important to the successful practice of the present invention. First, the film should have sufficient porosity (open area) so that the orthodontic bonding resin (adhesive) which is used to adhere the bracket to a tooth is allowed to flow freely and virtually unrestricted through the film to the chemically active bonding surface. Free flow of the orthodontic adhesive is important so that substantially 100% coverage of the bonding surface and intimate contact of the adhesive with the underlying bonding surface are achieved. This results in maximum chemical coupling, as if there were no protective film in place. In the ideal situation, the presence of the porous film should not affect the ultimate bond strength between the orthodontic appliance and the tooth; i.e., the protective film should not enhance or reduce the bond strength. In this regard, it is desired that the film not form a part of the bond structure, as that would tend to enhance or increase the bond strength. Conversely, it is desired that the film not provide a fracture plane (stress riser) wherein the weakest part of the bond is at the neck segments of adhesive which pass through the porous passages in the film. This latter situation is the subject of application Ser. No. 07/615,491, now U.S. Pat. No. 5,110,290. Finally, the film material should be essentially inert to orthodontic adhesives and body fluids so that chemical bonding, dissolution, discoloration, or degradation of the film does not occur.

In its broadest aspects, the orthodontic appliance of the present invention comprises a base portion having a chemically active bonding surface, and a protective porous film affixed to said base portion and substantially completely covering the bonding surface. The protective film possesses the general characteristics stated above and more fully detailed hereinafter in order to provide the degree of protection desired.

These and other advantages of the present invention will become apparent to persons skilled in the art upon reading the detailed description in conjunction with the drawings.

DETAILED DESCRIPTION OF THE INVENTION

Figure 1:
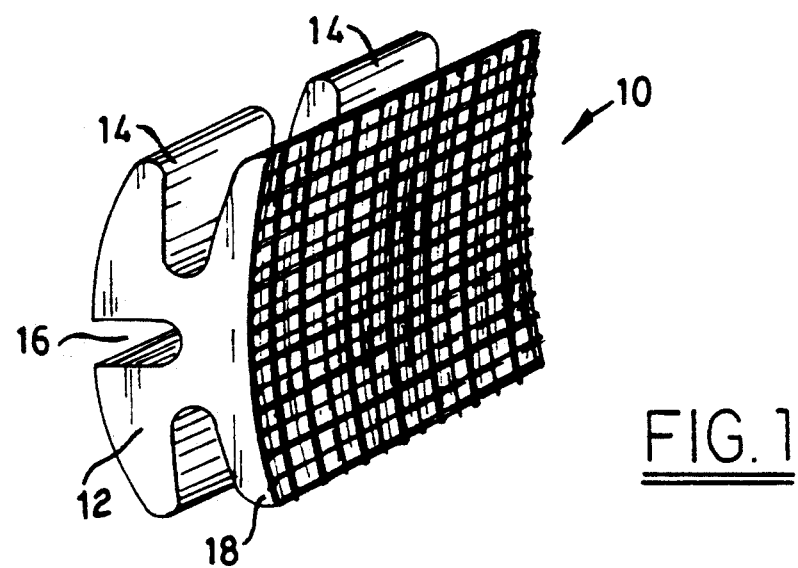
FIG. 1 is a perspective view of one embodiment of an orthodontic appliance of the present invention.

With reference to the Figures, there is illustrated an orthodontic appliance 10 in accordance with the present invention. In the particular embodiment illustrated, orthodontic appliance 10 is an orthodontic bracket. However, it is to be understood that orthodontic appliance 10 may be any other type of orthodontic appliance that is secured to a tooth. Since the appliance depicted is an orthodontic bracket, that terminology will be used henceforth. Orthodontic bracket appliance 10 comprises a main body portion 12, including a pair of twin tie wings 14 which define an archwire slot 16 for receiving a typical orthodontic archwire. Orthodontic bracket 10 further comprises a base portion 18 having a bonding surface 20 designed to be secured to a tooth. As is common in orthodontic brackets, bonding surface 20 may have a doubly curved concave surface such that the bracket primarily contacts the tooth at the four corners 28. It will be appreciated that a wide variety of bracket configurations are suitable in the practice of the present invention, but the present invention is not to be limited to an particular bracket construction. It will be further appreciated that bracket 10 may be metal, ceramic or plastic, depending on the circumstances of the particular patient treatment. The present invention is equally applicable to all types of brackets and materials, although it is particularly well suited for ceramic and plastic brackets. Brackets of each type of material (i.e., metal, ceramic, and plastic) are well known in the art.

Bonding surface 20 of orthodontic bracket 10 is a "chemically active" surface; i.e., the surface has been treated or modified by techniques known in the art to enhance chemical bonding of the bracket to a tooth with an orthodontic adhesive. The particular method for providing a chemically active bonding surface on a bracket does not form a part of the present invention; various techniques to accomplish this purpose are known for various bracket materials. For example, U.S. Pat. Nos. 4,826,430 and 4,948,366 describe ceramic brackets with chemically active bonding surfaces, and U.S. Pat. No. 4,673,354 discloses dental articles of dental porcelain, dental alloys and cured dental composites which have a chemically active layer. Thus, the present invention contemplates orthodontic appliances of ceramic, plastic or metal, having a suitable chemically active layer and a compatible protective porous film.

Figure 2:
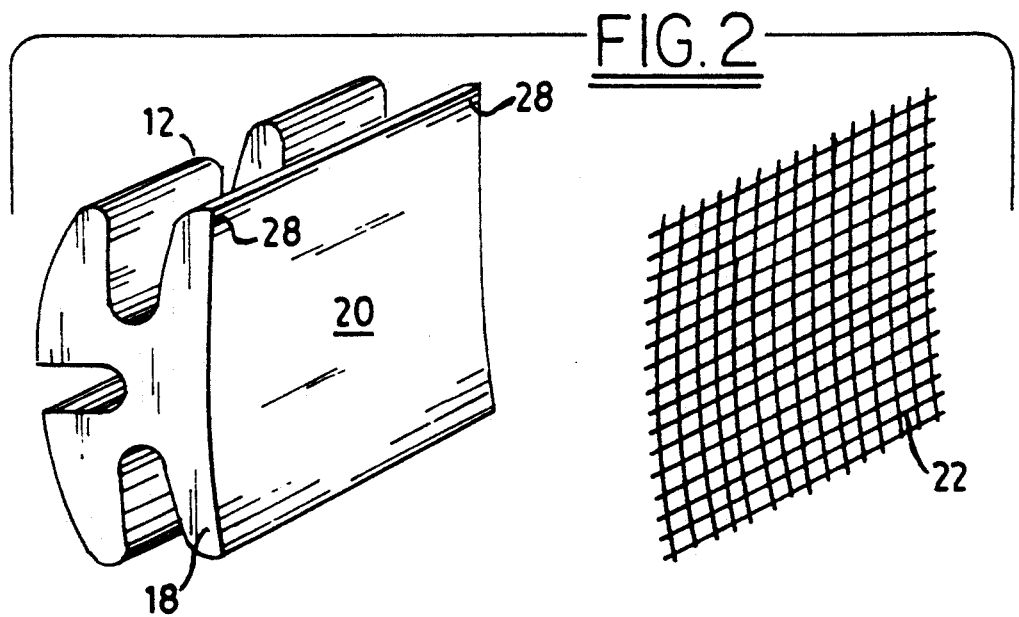
FIG. 2 is an exploded view of the orthodontic appliance of FIG. 1.

FIG. 2 shows an exploded view of an orthodontic bracket of the present invention with a porous film 22 in the form of a fabric of square mesh weave, which is applied over chemically active bonding surface 20 of bracket 10. In a preferred embodiment, polyester fabric of square mesh weave available from Tetko, Inc., Briarcliff Manor, N.Y. has been found to function suitably. In particular, the excellent protection of chemically active bonding surface 20 is achieved utilizing a mesh fabric having a thread diameter of approximately 40 microns (0.0015") to yield a fabric having a thickness of about 80 microns (0.003"), in a square weave configuration of approximately 60×60 mesh count per inch, resulting in an open area of about 70%. It will be appreciated, that a variety of polymeric materials other than polyester, filled or unfilled, will work equally well as the protective film in the present invention. For example, polypropylene, nylon, and polyethylene mesh fabrics available from Tetko of Briarcliff Manor, N.Y. are suitable. It will also be appreciated that various fabrics may be utilized which have thread size and mesh count different than that stated above, which is provided as an example and should not be construed as limiting the scope of the present invention.

For purposes of aesthetics, clear polymeric materials are preferred for the protective porous film; however, this is not critical to the present invention. The choice of materials for the porous protective film is defined primarily by the desirability that the protective layer be essentially inert to orthodontic adhesives, the chemically active layer of the bracket, and body fluids. This serves to prevent chemical bonding of the adhesive to the protective layer, and avoids dissolution, discoloration and/or degradation of the protective layer. A porous metallic film is also contemplated in the orthodontic appliance of the present invention.

An example of a suitable procedure for attaching a porous protective film to an orthodontic appliance is now described. First, the film is cut to match the configuration/shape of the bonding surface. Second, the film is positioned and clamped lightly in the center so that the film conforms to the contours, if any, of the bonding surface. Finally, an adhesive compatible with the film, or inert, is used to pin or tack the corners of the film in place. An example of a suitable tacking adhesive is Flourobond available from Ormco, Glendora, Calif.

It will be apparent to persons skilled in the art that various modifications can be made without departing from the scope of the present inventions. The examples provided herein are for illustrative purposes and are not to be construed as limiting the scope of the present invention, which is defined by the appended claims.

What is claimed is:

1. An orthodontic appliance for attachment to a tooth, said appliance comprising:
    a) a base portion having a chemically active bonding surface; and
    b) a porous protective film comprising a mesh fabric of a material substantially inert to orthodontic adhesives, said mesh fabric affixed to said base portion and covering substantially the entire bonding surface to prevent contamination thereof, said mesh fabric forms no part of a bond structure and does not form a fracture plane when said orthodontic appliance is affixed to a tooth with an orthodontic adhesive.

2. An orthodontic appliance of claim 1 wherein said mesh fabric is affixed to said bonding surface by an adhesive.

3. An orthodontic appliance of claim 1 wherein said mesh fabric comprises thread selected from the group consisting of polyethylene, polypropylene, nylon, and polyester.

4. An orthodontic appliance of claim 3 wherein said thread has a diameter in the range of about 20 to 60 microns.

5. An orthodontic appliance of claim 4 wherein said mesh fabric has a mesh count in the range of about 40×40 to 80×80 openings per inch.

6. An orthodontic appliance of claim 1 wherein said protective film is a porous metallic film.

* * * * *